(12) United States Patent
Reed et al.

(10) Patent No.: US 11,911,036 B2
(45) Date of Patent: Feb. 27, 2024

(54) STAPLE INSTRUMENT

(71) Applicant: Medline Industries, LP, Northfield, IL (US)

(72) Inventors: Wesley Reed, Libertyville, IL (US); Samuel Nader, Arlington Heights, IL (US); Dinesh Koka, Winter Park, FL (US)

(73) Assignee: Medline Industries, LP, Northfield, IL (US)

( * ) Notice: Subject to any disclaimer, the term of this patent is extended or adjusted under 35 U.S.C. 154(b) by 228 days.

(21) Appl. No.: 17/322,580

(22) Filed: May 17, 2021

(65) Prior Publication Data

US 2022/0361877 A1 Nov. 17, 2022

(51) Int. Cl.
*A61B 17/10* (2006.01)
*A61B 17/064* (2006.01)
(Continued)

(52) U.S. Cl.
CPC .......... *A61B 17/10* (2013.01); *A61B 17/0642* (2013.01); *A61B 17/0644* (2013.01); *A61B 17/0682* (2013.01); *A61B 2017/00367* (2013.01); *A61B 2017/00867* (2013.01); *A61B 2017/0409* (2013.01);
(Continued)

(58) Field of Classification Search
CPC . A61B 17/0642; A61B 17/0682; A61B 17/10; A61B 17/076; A61B 17/068; A61B 17/1775; A61B 17/1782; A61B 17/885; A61B 17/0644; A61B 17/68; A61B 17/92; A61B 17/8872; A61B 17/0684; A61B 2017/00367; A61B 2017/0645; A61B 2017/0409; A61B 2017/0412; A61B 2017/00867; A61B 2017/0648; A61B 2017/0646; A61F 2/4611; A61F 2/4603;
(Continued)

(56) References Cited

U.S. PATENT DOCUMENTS 3,960,147 A * 6/1976 Murray .............. A61B 17/8872
606/101
D337,159 S 7/1993 Hunt
(Continued)

FOREIGN PATENT DOCUMENTS

EP 3563776 11/2019

OTHER PUBLICATIONS

Arthrex, Inc. Dynanite Product Technique and Highlights Brochure, 2019.
(Continued)

*Primary Examiner* — Marcela I. Shirsat
(74) *Attorney, Agent, or Firm* — Fitch, Even, Tabin & Flannery LLP

(57) ABSTRACT

There is provided a staple instrument for inserting and removing staples from bone. A rotational drive shaft is turned to provide finite adjustments to open and close jaws used to hold and adjust the legs of a staple. A converter coupling converts the rotational motion of the drive shaft to liner motion to operate an articulated linkage system that moves the jaws. The jaws include a sharp edge to engage under a bridge of a staple inserted in bone segments and a convex pry surface that cooperates with the edge to pry a staple from the bone segments when the instrument is pulled away from the bone segments.

17 Claims, 17 Drawing Sheets

(51) Int. Cl.
  *A61B 17/00*  (2006.01)
  *A61B 17/04*  (2006.01)
  *A61F 2/46*  (2006.01)
  *A61F 2/08*  (2006.01)
  *A61B 17/068*  (2006.01)
  *A61F 2/30*  (2006.01)

(52) U.S. Cl.
  CPC ..... *A61B 2017/0645* (2013.01); *A61F 2/0811* (2013.01); *A61F 2/4603* (2013.01); *A61F 2002/30841* (2013.01)

(58) Field of Classification Search
  CPC ................. A61F 2/0811; A61F 2/0805; A61F 2002/30841
  USPC ................................................... 606/75, 151
  See application file for complete search history.

(56) References Cited

U.S. PATENT DOCUMENTS

| | | | |
|---|---|---|---|
| 6,089,435 A * | 7/2000 | Malek | B25C 5/025 227/63 |
| 8,137,351 B2 | 3/2012 | Prandi | |
| 9,095,338 B2 | 8/2015 | Taylor | |
| 9,855,036 B2 | 1/2018 | Palmer | |
| 9,861,413 B2 | 1/2018 | Palmer et al. | |
| 10,064,619 B2 | 9/2018 | Palmer | |
| 10,130,358 B2 | 11/2018 | Palmer | |
| 10,610,218 B2 | 4/2020 | Palmer et al. | |
| 10,945,725 B2 | 3/2021 | Hollis | |
| 11,284,887 B2 | 3/2022 | Hartdegen | |
| D977,640 S | 2/2023 | Ritz | |
| 11,596,398 B2 | 3/2023 | Wahl | |
| 2016/0199060 A1 * | 7/2016 | Morgan | A61B 17/10 227/175.1 |
| 2017/0296174 A1 * | 10/2017 | Wahl | A61B 17/068 |
| 2018/0271521 A1 | 9/2018 | Wahl | |
| 2018/0317906 A1 | 11/2018 | Hollis et al. | |
| 2018/0344316 A1 | 12/2018 | Palmer | |
| 2022/0361877 A1 | 11/2022 | Reed | |
| 2023/0027093 A1 | 1/2023 | Wahl | |
| 2023/0200809 A1 | 6/2023 | Wahl | |

OTHER PUBLICATIONS

CrossRoads® Extremity Systems, LLC Announces Launch of the DynaFORCE™ Dynamic Compression Fixation System, https://www.crextremity.com/crossroads-extremity-systems-llc-announces-launch-of-the-dynaforce-dynamic-compression-fixation-system/, dated Jul. 11, 2017.
DePuy Synthes, BME Elite Implant Technique Overview, 2017.
DePuy Synthes, Speed Memory Implant Brochure, 2016-2018.
MedShape, Inc., Dynaclip Fixation System, Surgical Technique Guide, 2019.
NeoSpan Food, In2Bones, https://web.archive.org/web/20170410093305/http:/i2b-usa.com/neospan-foot/, 2017.
NeoSpan SE Compression Staples, https://i2b-usa.com/neospan-se-compression-staple/, 2021.
Paragon 28, Inc., Surgical Technique Guide: JAWS Nitinol Staple System Brochure, 2020.
Stryker Corporation, "EasyClip Osteosynthesis Compression Staples," 2012.
Stryker Corporation, "EasyClip Osteosynthesis Compression Staples," 2015.
U.S. Food & Drug Administration, 510(k) Premarket Notification, https://www.accessdata.fda.gov/scripts/cdrh/cfdocs/cfpmn/pmn.cfm?ID=K161426, Oct. 24, 2016.

* cited by examiner

STAPLE INSTRUMENT

FIELD

The disclosure relates to medical instruments and, more particularly, to a medical instrument for inserting, removing and adjusting staples into bones.

BACKGROUND

Many surgical procedures take place requiring bone tissue to form between bone segments. The ability for successful bone tissue growth at the site of the bone segments is improved when the bone segments are under compression. If there is no compression, a gap may form between the bone segments. These gaps tend to lengthen the healing time or impede complete healing. One method to achieve compression is the use of compression staples. Compression staples include a pair of legs interconnected by a bridge. These staples are commonly made from material having memory, such as a nitinol alloy, so that when the legs are splayed, they want to return to their natural position.

There is a desire for an instrument that can hold and spread the legs of a compression staple for insertion into drilled holes in adjacent bone segments. There also is a desire for the instrument to be capable of lifting or even removing the staple for repositioning of the staple in the bone segments.

DETAILED DESCRIPTION

Figure 1:
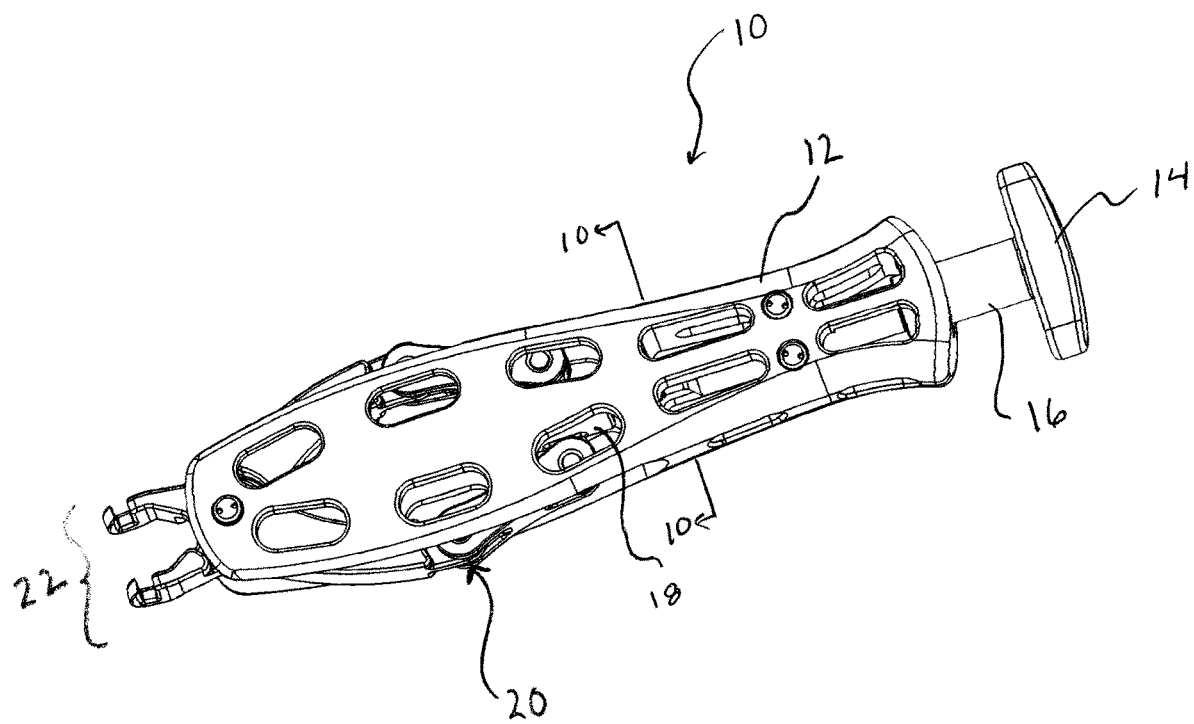
FIG. 1 is a perspective view of a staple instrument.

With reference to FIG. 1, there is illustrated an instrument 10 for inserting a staple to provide fixation for bone fractures or fusions or osteotomies of the bones. The instrument 10 includes in general a body or housing 12, a handle 14, a drive shaft 16, a converter coupling such as nut 18, a linkage mechanism 20, and a staple holder 22. The drive shaft 16 is operatively coupled to the linkage mechanism 20 through the nut 18. A distal end of the linkage mechanism 20 includes the staple holder 22. When one turns the handle 14 clockwise, the drive shaft 16 drives the nut 18 away from the handle 14, which causes the linkage mechanism 20 to spread. This spreading expands the staple holder 22 which, in turn, spreads a set of legs of the staple for insertion into a bone. A staple typically includes a pair of spaced legs interconnected on one end by a bridge. As one turns the handle 14 counterclockwise, the drive shaft 16 draws the nut 18 toward the handle 14 and collapses the linkage mechanism 20. This causes the staple holder 18 to contract to release a staple.

Figure 2:
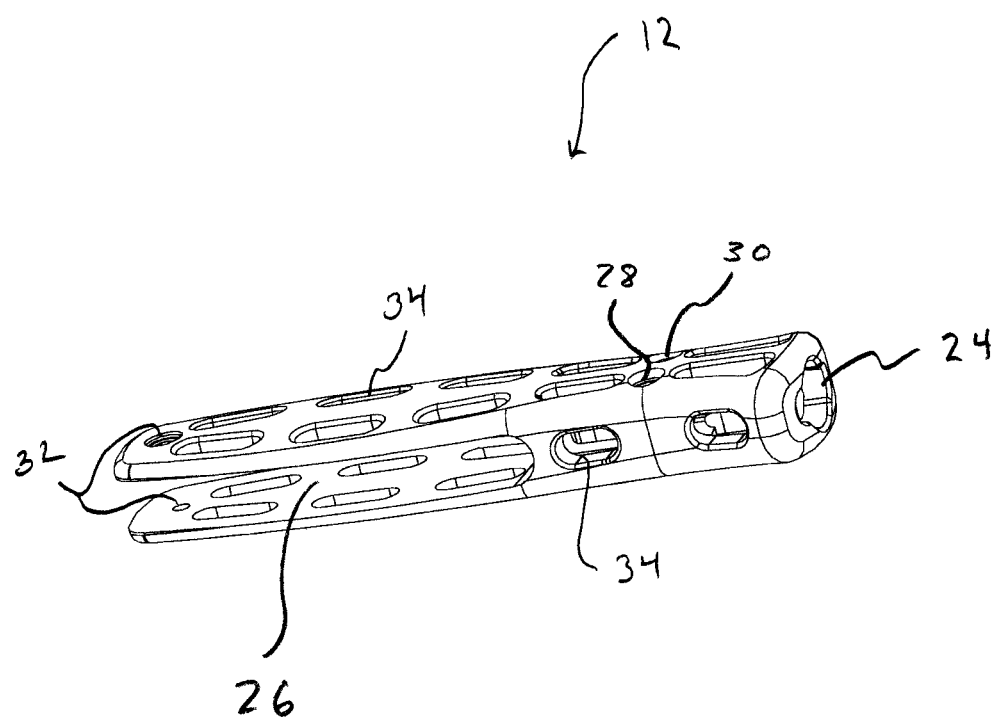
FIG. 2 is a perspective view of a body of the staple instrument of FIG. 1.
Figure 3:
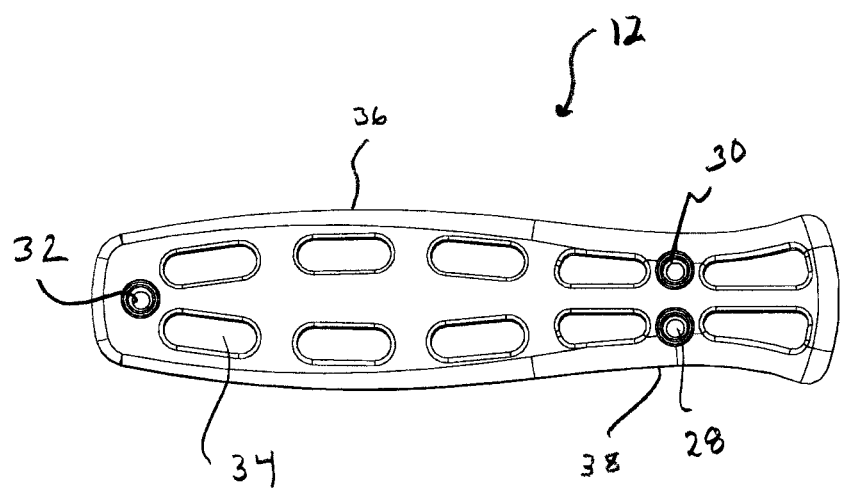
FIG. 3 is a plan view of the body of FIG. 2.

Turning to FIGS. 2-3, the body 12 defines a drive shaft opening 24 at one end and a yoke 26 at the other end. The drive shaft 16 extends through the opening 24 into the body 12 to operatively couple to the nut 18 in the body 12. The linkage mechanism 20 operates in the yoke 26. As explained in further detail below, the body 12 defines three pairs of anchor holes, two 28, 30 for pinning the drive shaft 16 against axial movement and one 32 for providing a hinge point for the linkage mechanism 20. The openings into the holes can be enlarged to enable countersinking the ends of the fasteners flush with body 12.

The body 12 defines apertures 34 that are used during the cleaning and sterilization processes. The instrument 10 may be made from material that may be subject to conventional cleaning and sterilization methods, such as steam, gas, and radiation sterilization methods. For example, the body may be made from a titanium alloy, and the other components may be made from stainless steel. Alternatively, the body and other components may be made of any material that is permitted for surgical instruments. The apertures 34 enable cleaning instruments, cleaning solutions, steam, gas and/or radiation to penetrate inside the body 12 to sterilize all surfaces of the instrument 10. The apertures 34 are shown with an oval like shape; however, other shapes, such as circular, triangular, rectangular, etc. may be employed to allow cleaning instruments, cleaning solutions, steam, gas and/or radiation to access the surfaces of the instrument 10 inside the body 12. The body 12 may be a one-piece structure and may be made from milling or additive manufacturing.

The profile of the body may be designed to conform ergonomically to a user's hand. For example, the profile of the body 12 may have a convex portion 36 along the yoke 26 and a concave portion 38 at the anchor holes 28, 30. The convex portion 36 may be longer than the concave portion 38.

Figure 4:
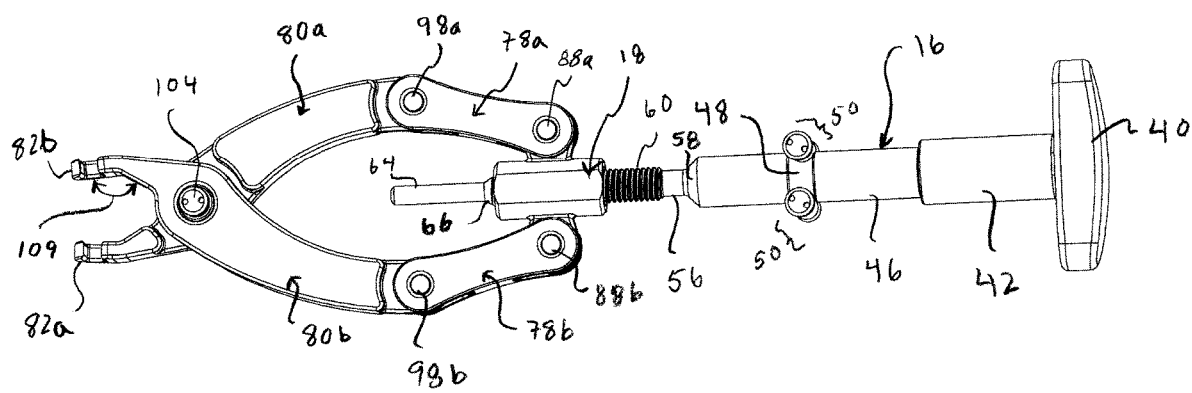
FIG. 4 is a plan view of staple instrument of FIG. 1 with the body removed.
Figure 5:
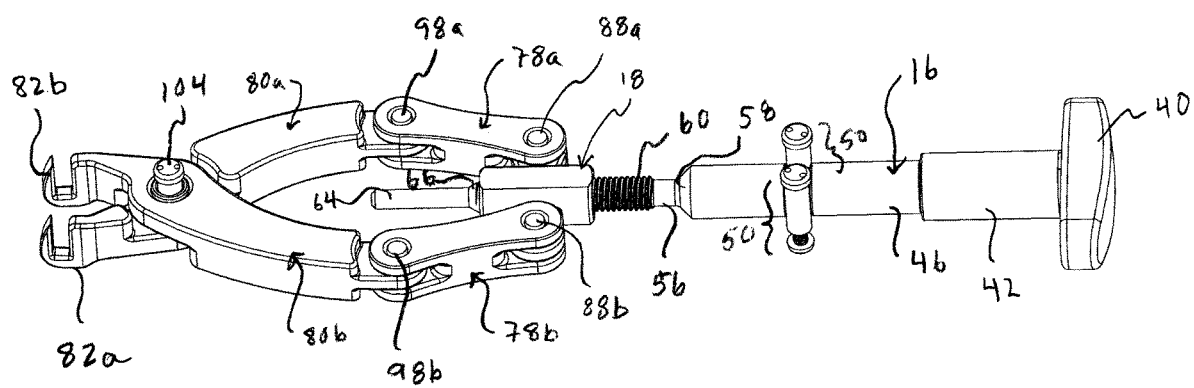
FIG. 5 is a perspective view of the staple instrument of FIG. 1 with the body removed.
Figure 6:
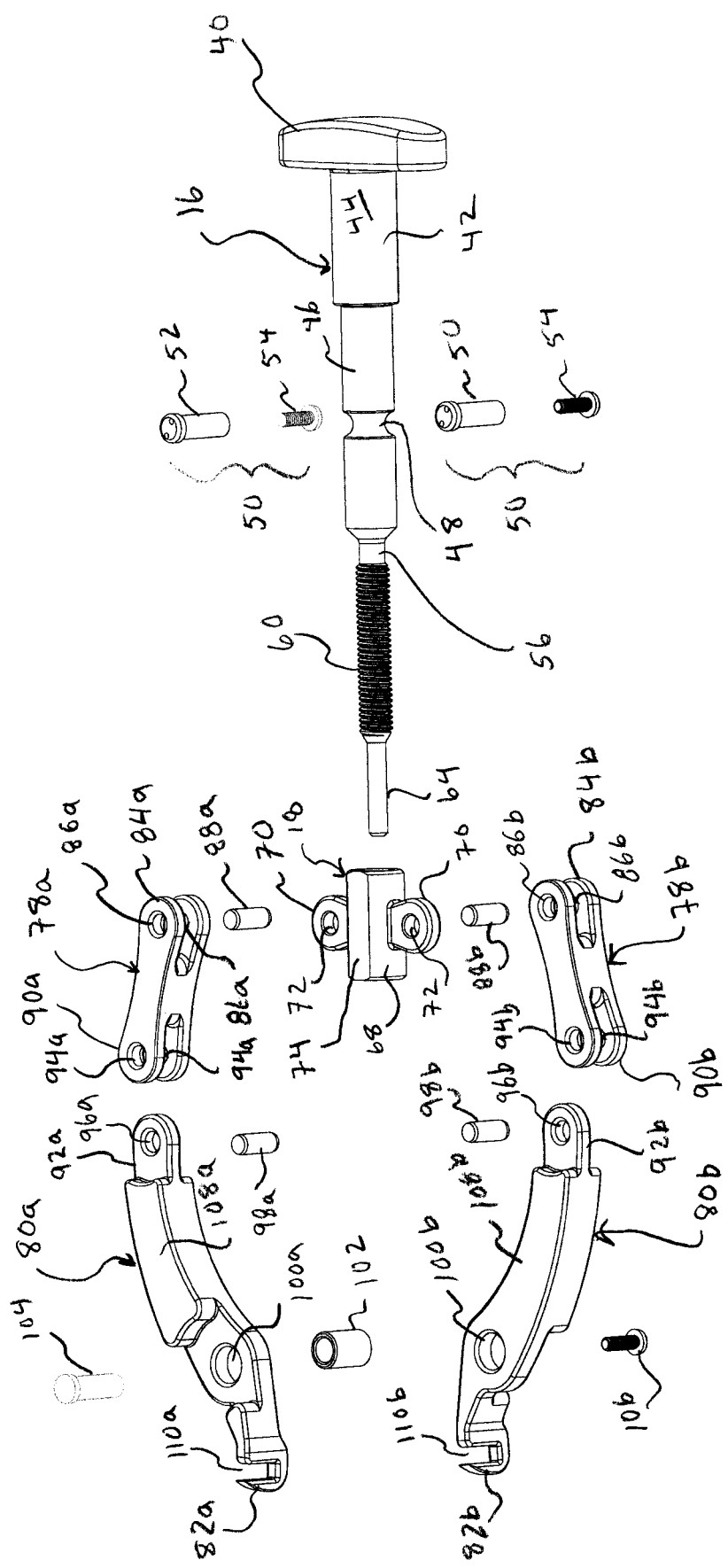
FIG. 6 is an exploded view of the staple instrument of FIG. 1 with the body removed.

With reference to FIGS. 4-6, the drive shaft 16 includes a handle and four axially aligned segments extending in series away from the handle 40. The handle 40 forms a T-shape with the first segment 42. The first segment 42 extends through the shaft opening 24 of the body 12 and is manually turned by operating the handle to rotate in the shaft opening 14. The first segment 42 includes a smooth outer surface 44.

The second segment 46 extends from the first segment 42 and has a diameter less than a diameter of the first segment 42. The second segment 46 defines an annular groove 48 intermediate it ends. A pair of fasteners 50 extending through the anchor holes 28, 30 of the body 12 reside in diametrically opposite portions of the annular groove 48 to prevent axial movement of the drive shaft 16 relative to the body 12. Each fastener 50 includes an internally threaded boss 52 and an externally threaded screw 54. The annular groove 48 has a smooth surface, and each boss includes a smooth outer surface that engages and slides against the smooth surface of the annular groove 48 with minimal friction resistance and play for accurate turning of the drive shaft 16.

Figure 7:
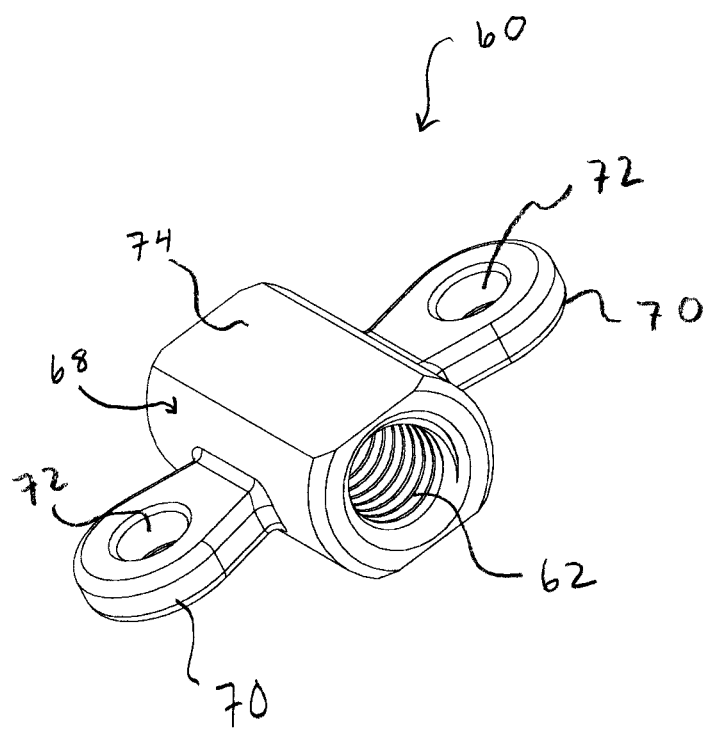
FIG. 7 is a perspective view of a nut of the staple instrument of FIG. 1.
Figure 8:
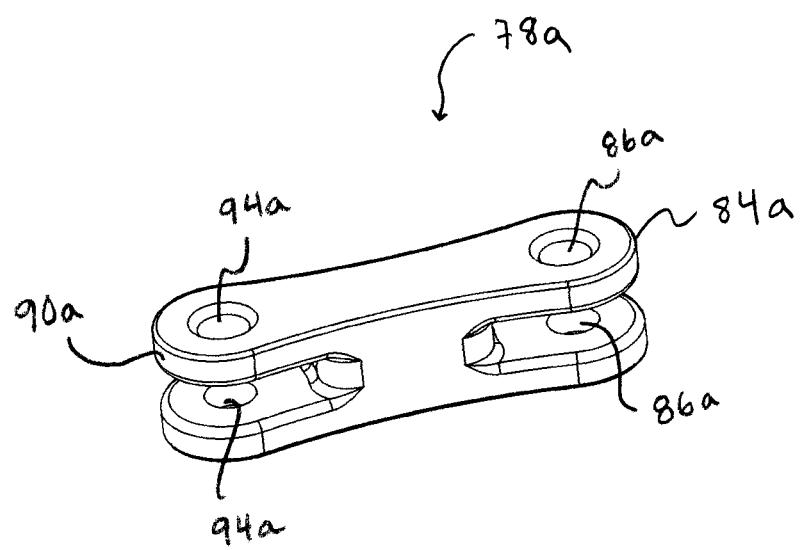
FIG. 8 is a perspective view of a first link of the staple instrument of FIG. 1.
Figure 9:
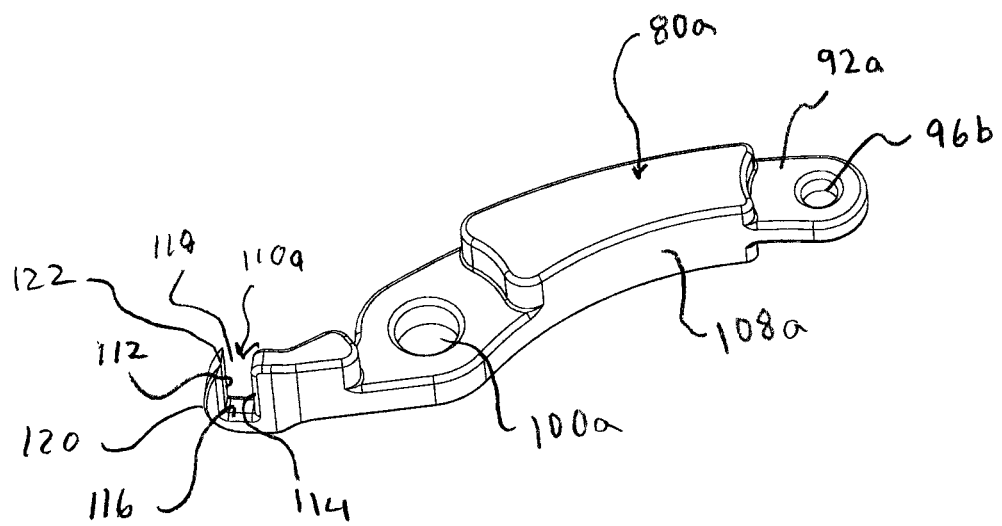
FIG. 9 is a perspective view of a second link of the staple instrument of FIG. 1.

The third segment 56 extends from the second segment 46 and has a diameter less than the diameter of the second segment 46. The transition between the second segment 46 and third segment 56 forms an annular chamfer 58. The third segment 56 includes an externally threaded portion 60 that cooperates with an internally threaded bore 62 in the nut 18 (FIG. 7). The threading of the threaded portion 60 and the threaded bore 62 may be left-handed threading. This enables clockwise rotation of the handle 40 to splay the legs of the staple. Alternatively, the threading could be right-handed to enable counterclockwise rotation of the handle to splay the legs of the staple.

The fourth segment 64 extends from the third segment 56 and has a diameter less than the diameter of the third segment 56. The transition between the third segment 56 and the fourth segment 64 forms an annular chamfer 66. The instrument 10 may need to be cleaned and sterilized between uses. This is a two-step process, where the first step is the cleaning, and second step is the sterilization. The annular chamfer 66 provides access into the nut 18 for cleaning instruments, cleaning solutions, steam, gas (e.g., ethylene oxide), and radiation (e.g., gamma radiation) during the cleaning and sterilization processes when the third segment 56 is backed out of the nut 18. The chamfer 66 provides a gap so that cleaning instruments, cleaning solutions, steam, gas, and/or radiation can penetrate the threaded bore 62. The diameter of the fourth segment 64 is less than an inner diameter of the threaded bore 62 so that cleaning instruments, cleaning solutions, steam, gas and/or radiation can reach all the internal surfaces of the threaded bore 62. The fourth segment 64 does not back out of the threaded bore 62 of the nut 18. This continued extension into the threaded bore 62 coupled with the annular chamfer 66 provide a guide to reengage the threaded portion 60 of the third segment 56 with the threaded bore 62 for operation of the instrument 10 after cleaning and sterilization. An outer surface of the fourth segment 64 may be smooth so not to damage the threading of threaded bore 62. The stepped down configuration of the drive shaft 16 helps to keep the desired size of the instrument 10.

Figure 10:
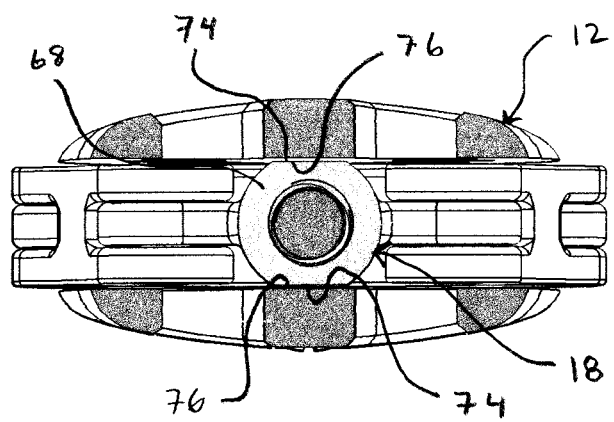
FIG. 10 is a cross-section view of the staple instrument of FIG. 1 taken along line 10-10 of FIG. 1.

As shown in FIGS. 4-7, the nut 18 includes a body 68 defining the threaded bore 62. A pair of lobes 70 extend from diametrically opposite sides of the body 68, and each lobe 70 defines a hole 72 for use in attachment to the linkage mechanism 20. The body 68 includes opposing flats 74 that engage flat surfaces 76 on an inside surface of the body 12 to guide reciprocating movement of the nut 18 during operation of the instrument 10 (FIG. 10). The engaging flats 74, 76 also prevent rotation of nut 18 during operation.

The linkage mechanism 20 includes two sets of articulated links. Each set of links includes a first link 78a, 78b that connects to the nut 18 and a second link 80a, 80b that connects to the first link 78a, 78b and includes a staple jaw 82a, 82b. The first links 78a, 78b are generally linear. One end of the first link 78a, 78b defines a yoke 84a, 84b that receives one of the lobes 70 of the wing nut 18. The yokes 84a, 84b define holes 86a, 86b that align with the hole 72 in the lobes 70. A pin 88a, 88b extends through the aligned holes 72, 84a, 84b to secure the lobe 70 in the yokes 84a, 84b with a connection that allows the first links 78a, 78b to pivot relative to the nut 18. Ends of the pins 88a, 88b may be laser welded to lock them in the yoke 84a, 84b and may be flush with or below an outer surface of the yokes 84a, 84b.

The other end of the first link 78a, 78b defines a yoke 90a, 90b that receives a tab 92a, 92b of second link 80a, 80b. The yokes 90a, 90b define holes 94a, 94b that align with a hole 96a, 96b defined by the tabs 92a, 92b, respectively. A pin 98a, 98b extends through the aligned holes 94a, 96a and 94b, 96b to secure the tab 92a, 92b in the yokes 94a, 94b, respectively, with a connection that allows the first links 78a, 78b and the second links 80a, 80b to pivot relative to one another. Ends of the pins 98a, 98b may be laser welded to lock them in the yoke 94a, 94b and may be flush with or below an outer surfaces of the yokes 84a, 84b.

The second links 80a, 80b each define a hole 100a, 100b that align with one another and the hinge hole 32 of the body 12. A boss 102 extends through the holes 100a, 100b and a shaft 104 with an internally threaded bore extends into the boss 102 and a screw extends into the internally threaded bore of the shaft 104 to secure the second links 80a, 80b against movement relative to the body 12 of the instrument 10. The second links 80a, 80b pivot about the boss 102 during operation of the instrument 10.

The second links 80a, 80b include an arcuate segment 108a, 108b between the holes 96a, 96b and 100a, 100b. The tabs 92a, 92b may have a reduced thickness relative to the arcuate segment 108a, 108b. The portion of the second links 80a, 80b defining the holes 100a, 100b also may have a reduced thickness. The reduced thickness enables the linkage mechanism to be compact and operate in generally the same plane.

The second links 80a, 80b terminate with the staple hooks 82a, 82b. The staple hooks 82a, 82b extend at an offset from the remainder of the second link 80a, 80b. The extent of the offset is denoted with an angle 109 (FIG. 4). The angle 109 may be predetermined for a particular staple size or range of staple sizes. It is preferred that the hooks remain generally parallel with the bridge of the staple so that the instrument 10 can insert the staple to a maximum depth into the bone. More specifically, when staple jaws are moved away from one another they may turn (i.e., move out of parallel) with the bridge of the staple. This turning would not allow the instrument 10 to set the staple as far into the bone as when the staple jaws remain parallel with the bridge.

For example, one offset angle 109 may be 145 degrees, which has been found to work effectively with staples having a bridge length ranging from 15-25 millimeters and a leg length ranging from 15-20 millimeters. Exemplary staples for use with the instrument 10 may include 15×15, 15×18, 18×18, 18×20, 20×20, and 25×20. The first number represents the length of the bridge in millimeters, and the second number represents the length of the legs in millimeters.

The offset angle can be reduced for larger staples and increased for smaller staples. Also, the length of the staple jaws can be increased or decreased depending on the size of the staples. Further, the instrument 10 itself can be scaled down in size to accommodate smaller staples or scaled up in size to accommodate larger staples.

Each staple jaw 82a, 82b defines a recess 110a, 110b for receiving the bridge of the staple. Each recess 110a, 110b includes a bottom surface 112, a top surface 114, a side surface 116 interconnecting the bottom and top surfaces 112, 114, and an opening 118 opposite the side surface 116 for receiving the staple. Each of the surfaces 112, 114, 116 may be flat and may provide the recess 110a, 110b with a generally rectangular shape. In connection with the offset angle 109 explained above, it is the bottom surface 112 of the staple jaws 82a, 82b that is desired to remain parallel with the bridge of the staple. The staple jaws 82a, 82b engage the legs of the staple to splay legs for insertion into bone segments.

Figure 11:
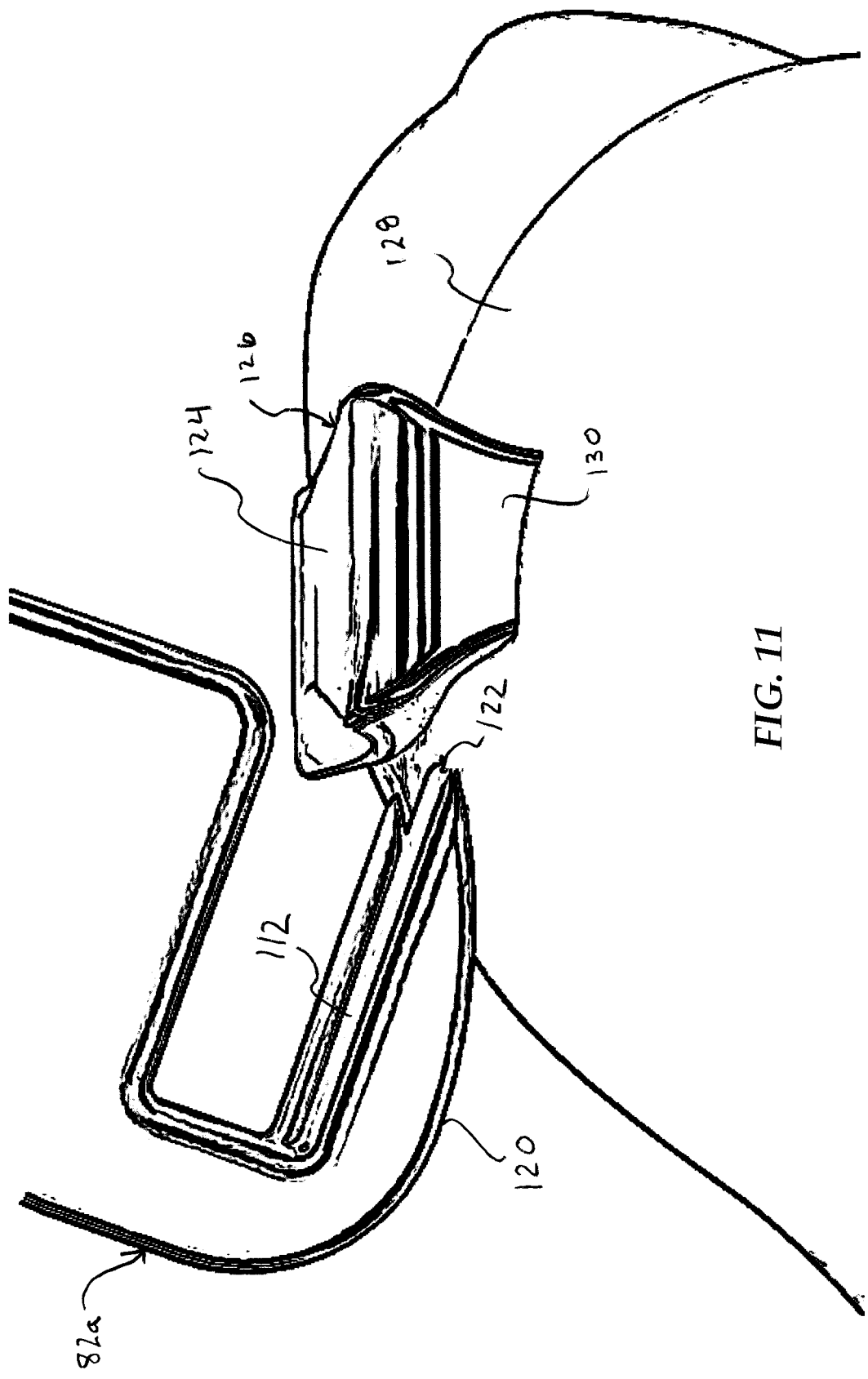
FIG. 11 is an elevation view of staple jaws of the staple instrument of FIG. 1 being positioned to remove a staple from a bone.

With reference to FIG. 11, the bottom of the staple jaw 82a, 82b may include a convex surface 120 that meets with the bottom surface 112 along an edge 122. The edge 122 and the convex surface 120 may be used to remove staples from bone segments. For instance, the edge 122 may be used to insert the staple jaw 82a, 82b under the bridge 124 of a staple 126 in a bone 128, and the instrument 10 then may be pivoted back over the convex surface 120 to pry legs 130 of the staple 126 from the bone 128.

Figure 12:
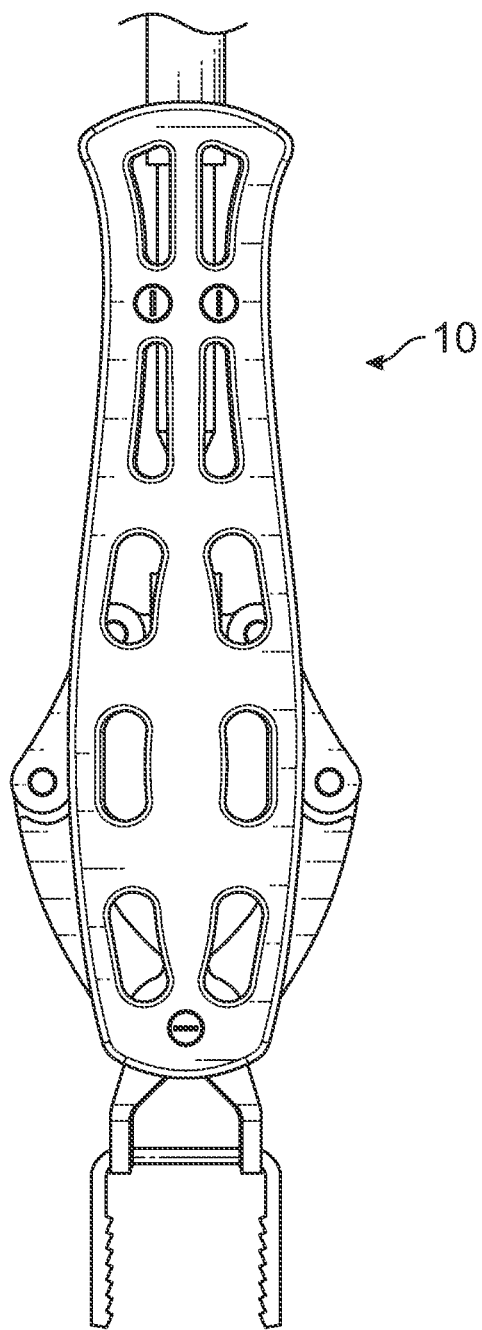
FIG. 12 is an elevation view of the staple instrument of FIG. 1 holding a staple for insertion into a bone.
Figure 13:
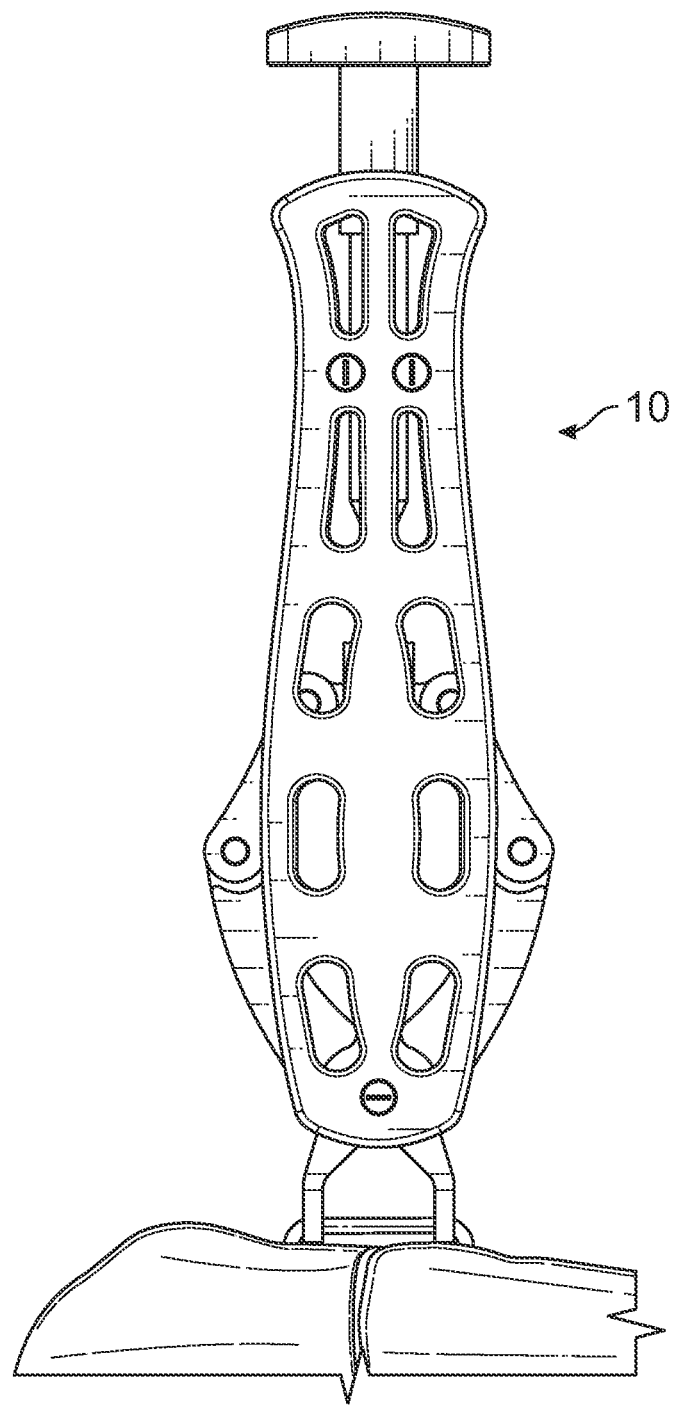
FIG. 13 is an elevation view of the staple instrument of FIG. 1 inserting a staple into a bone.

FIG. 12 illustrates the instrument 10 holding a staple. The bridge of the staple is being held in the jaws 82a, 82b. The jaws 82a, 82b are located adjacent the transition between the bridge and the legs of the staple. In FIG. 12, the instrument 10 is holding the legs outward in a parallel position. FIG. 13 illustrates the instrument 10 being used to insert a staple into the bone 128. The instruments 10 and 210 may be used to insert and remove a staple using any accepted technique.

Figure 14:
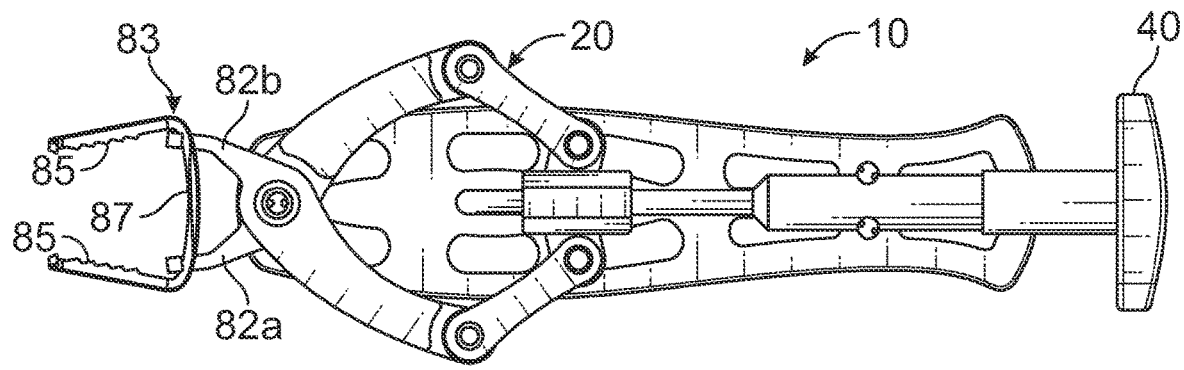
FIG. 14 is an elevation view of the staple instrument of FIG. 1 in an initial position for loading a staple.
Figure 15:
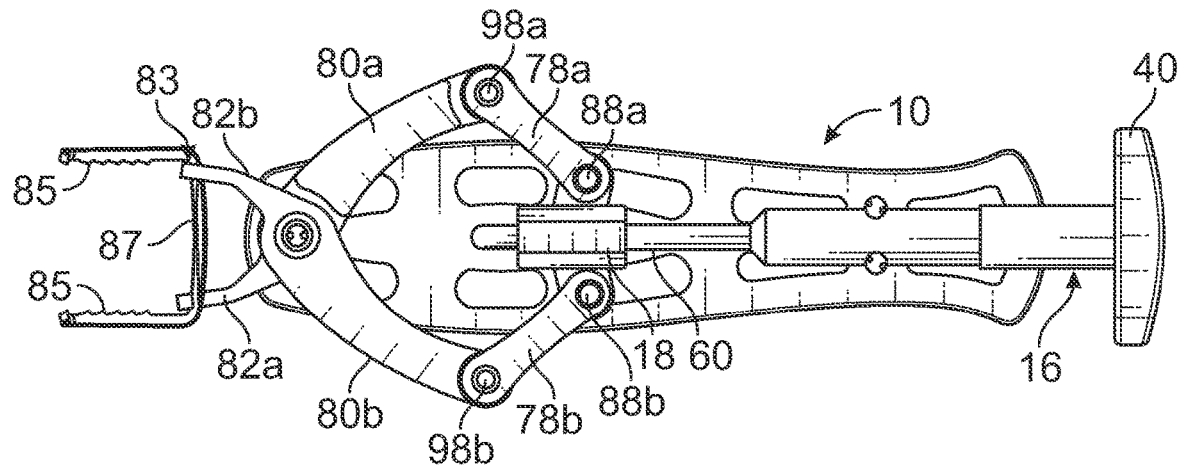
FIG. 15 is an elevation view of the staple instrument of FIG. 1 in a staple insert position with legs of a staple parallel to one another.
Figure 16:
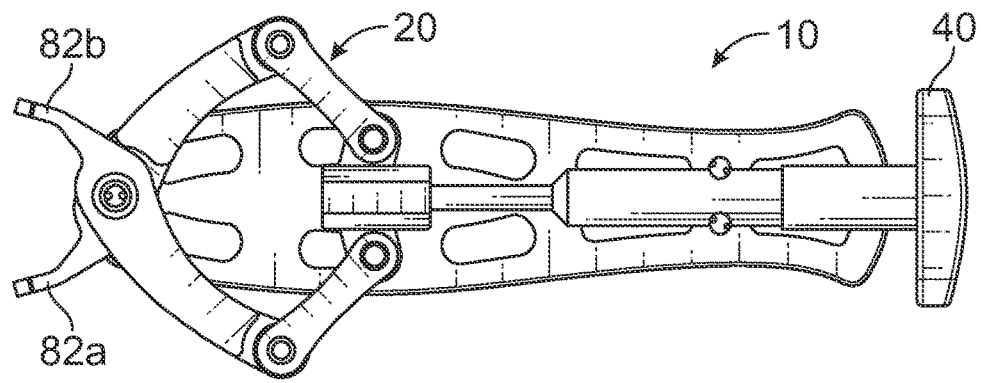
FIG. 16 is an elevation view of the staple instrument of FIG. 1 in a fully opened position.

FIGS. 14-16 show three different positions of the instrument 10. More specifically, FIG. 14 shows the instrument 10 in an initial position for loading a staple 83. In this initial position, the staple jaws 82a, 82b are spaced apart to be positioned at a transition between a pair of legs 85 and a bridge 87 of the staple 83. The staple 83 is then loaded in the staple jaws 82a, 82b.

FIG. 15 shows the instrument 10 in an intermediate position where the linkage mechanism 20 is opened more than in FIG. 14, thereby moving the staple jaws 82a, 82b away from one another. This position is achieved by turning the handle 40 clockwise to force the nut 18 toward the staple jaws 82a, 82b. The first links 78a, 78b pivot about the pins 88a, 88b at the nut 18 and drive the second links 80a, 80b outward, pivoting about the pins 98a, 98b. This outward movement of the second links 80a, 80b splays the staple jaws 82a, 82b, which, in turn, move the legs 85 from their initial inward directed position to a position where they are parallel or nearly parallel with one another. In this parallel or nearly parallel position, the legs 85 can be inserted into holes in bone segments. The treaded portion 60 of the drive shaft 16 enables very infinite adjustments from the initial position of FIG. 14 to many different intermediate positions, such as the one in FIG. 15.

FIG. 16 shows the instrument 10 in a fully opened position where the linkage mechanism 20 is at its most expanded state, thereby positioning the staple jaws 82a, 82b at their maximum distance away from one another. The fully opened position is achieved by turning the handle 40 further in the clockwise direction. The operation of the instrument 10 is the same as discussed above for FIG. 15. For sterilization of the instrument 10, the handle 40 may be turned even further clockwise to draw the threaded portion 60 of the drive shaft 16 out from the nut 18. This enables the surfaces in the nut 18 to be exposed for sterilization. The fourth section of the drive shaft 16 remains in the nut 18 during sterilization.

To reengage the drive shaft 16 with the nut 18, one uses the handle 40 to align the chamfer 66 of the drive shaft 16 with the threaded bore 62 of the nut 18 and turns the handle 40 counterclockwise. Once the threads of the threaded portion 60 and the threaded bore 62 engage, continued counterclockwise rotation of the handle 40 moves the instrument 10 from the fully opened position to the initial position.

Figure 17:
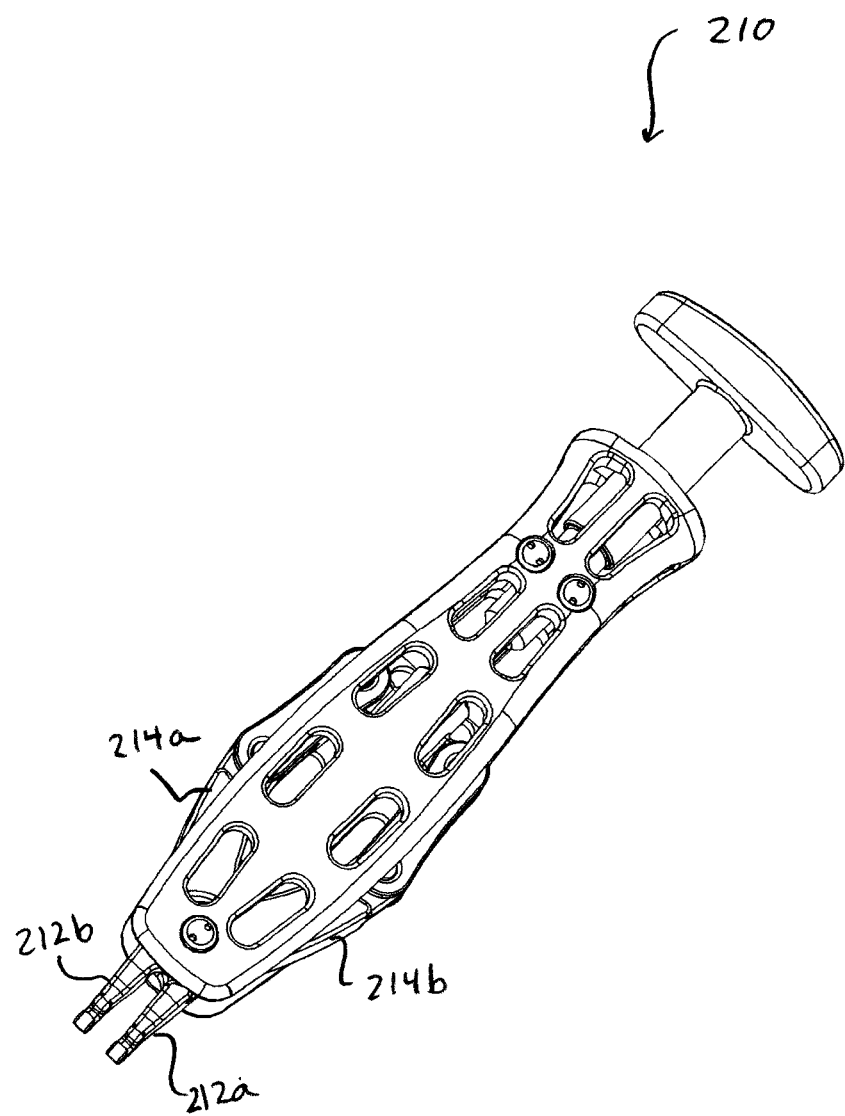
FIG. 17 is a perspective view of another staple instrument.
Figure 18:
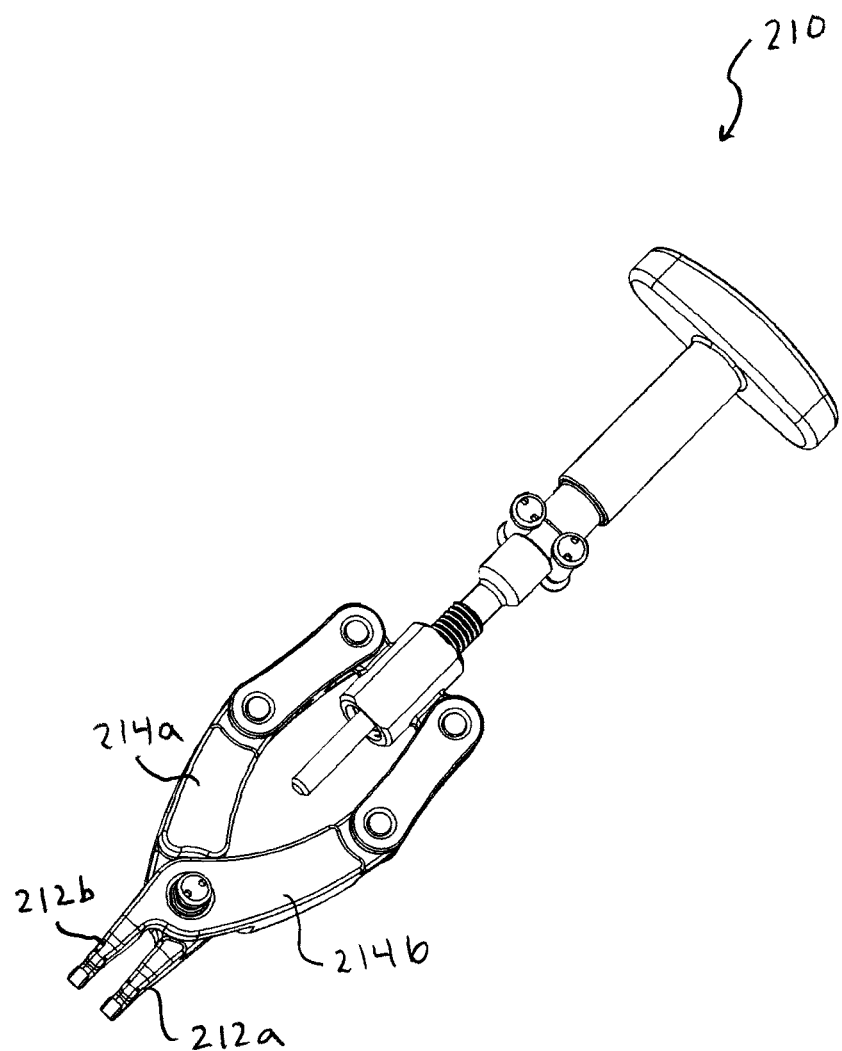
FIG. 18 is a perspective view of the staple instrument of FIG. 17 with the body removed.

Regarding FIGS. 17-18, there is illustrated an alternative instrument 210 for inserting staples into a bone. The instrument 210 is identical in structure and function to the instrument 10 described herein except that the staple jaws 212a, 212b are not offset like the jaws 82a, 82b. The staple jaws 212a, 212b extend generally more straight from the second link 214a, 214b. The instrument 210 may work more effectively for smaller staples, such as 8×8, 10×10, and 12×12 staples. Like above, the first number represents the length of the bridge in millimeters, and the second number represents the length of the legs in millimeters.

Figure 19:
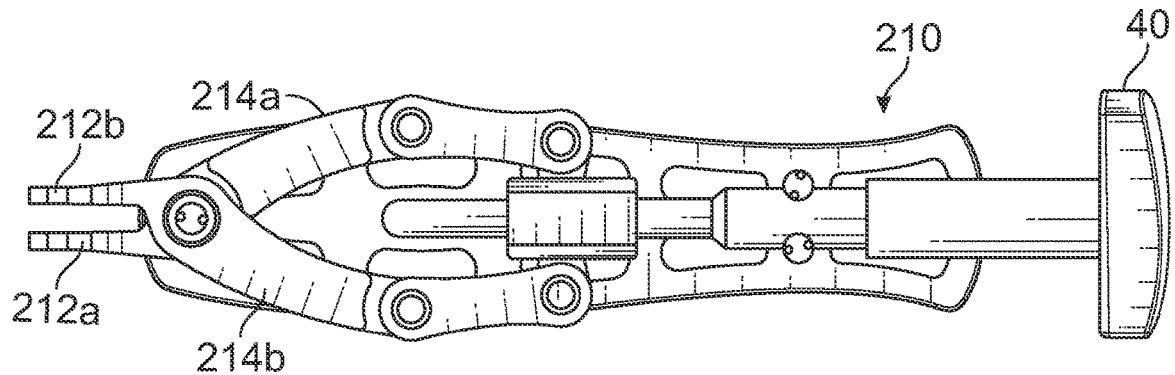
FIG. 19 is an elevation view of the staple instrument of FIG. 17 in an initial position for loading a staple.
Figure 20:
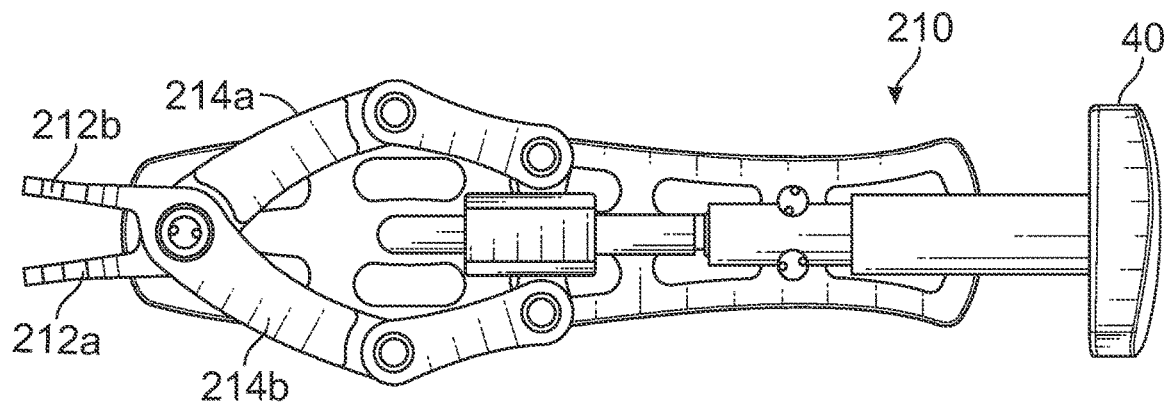
FIG. 20 is an elevation view of the staple instrument of FIG. 17 in an intermediate position.
Figure 21:
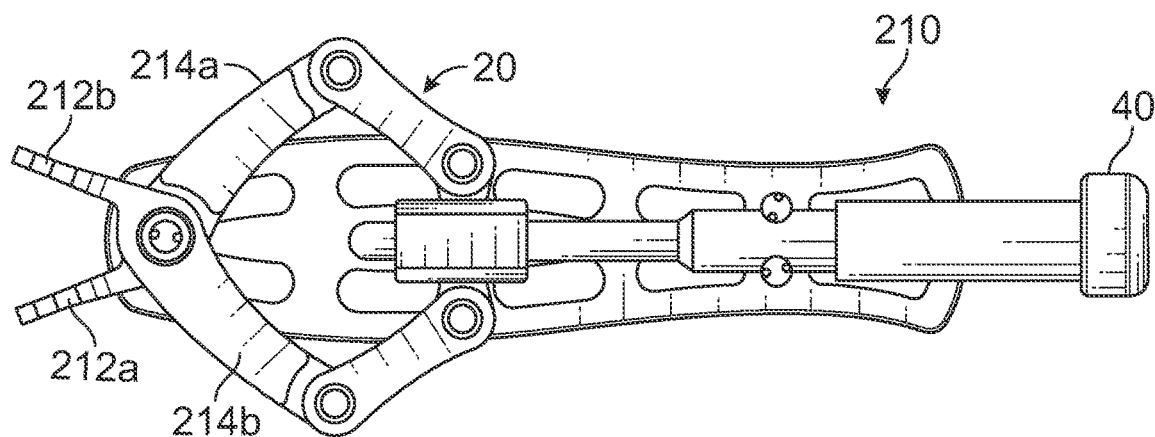
FIG. 21 is an elevation view of the staple instrument of FIG. 17 in a fully opened position.

FIGS. 19-21 show three different positions of the instrument 210. More specifically, FIG. 19 shows the instrument 210 in an initial position. In this initial position, the staple jaws 212a, 212b are spaced in a relatively close position such as a position for loading a staple.

FIG. 20 shows the instrument 210 in an intermediate position where the linkage mechanism 20 is opened more than in FIG. 19, thereby moving the staple jaws 212a, 212b away from one another. This position is achieved by turning the handle 40 clockwise to force the nut 18 toward the staple jaws 212a, 212b. The linkage operation works the same as that described herein for instrument 10.

FIG. 21 shows the instrument 210 in a fully opened position where the linkage mechanism 20 is at its most expanded state, thereby positioning the staple jaws 212a, 212b at their maximum distance away from one another. The fully opened position is achieved by turning the handle 40 further in the clockwise direction. The operation of the instrument 210 is the same as discussed above for instrument 10.

There are many surgical procedures in which the instruments 10, 210 may be employed to insert or remove staples. An example of one procedure includes the following steps with reference to instrument 10. This procedure applies equally to instrument 210.

A surgeon first selects the staple size most appropriate for the patient's anatomy along with the corresponding drill guide. Then, the drill guide is placed against the bone with the closed osteotomy positioned centrally between the two drill sleeves. A drill bit is used to drill through the proximal drill sleeve, and with the drill guide still in position, the surgeon places a locator pin through the proximal drill sleeve and into the pre-drilled hole to maintain position, With the osteotomy held in a closed position, the surgeon drills through the distal drill sleeve and places a second locator pin the hole. Next, the pin placement is verified visually and fluoroscopically, as the locator pins will indicate definitive positioning of the staple legs.

To load the staple in the instrument 10, 210, the surgeon turns the handle 40 counterclockwise to contract the staple jaws 82a, 82b, allowing them to fit under the staple bridge and between the staple legs. Next, the surgeon turns the handle clockwise so the staple jaws 82a, 82b grasp and retain the staple. The handle 40 is twisted further in the clockwise direction until the staple legs are parallel or nearly parallel. A laser marked sizing gauge on the staple caddy may be used to verify that the staple legs are in the parallel or nearly parallel position. Now, the locator pins are removed from the pre-drilled staple leg holes, ensuring that the osteotomy is maintained in a closed position. With the instruments 10, the staple legs are advanced into the pre-drilled holes until the staple jaws 82*a*, 82*b* are flush with the bone, and then, the handle 40 is turned counterclockwise to release the staple. Finally, a tamp and mallet are used to seat the bridge of the staple flush with the bone and placement is verified visually and fluoroscopically. If the staple requires repositioning or removal, the sharp jaw edge 122 of the staple jaw 82*a*, 82*b* allows the surgeon to pry, expand and lift the staple from its seated position.

The staple instruments 10, 210 may be provided in a container. The container may also include at least one of a drill guide, a staple, a pin, and a tamp.

The matter set forth in the foregoing description and accompanying drawings is offered by way of illustration only and not as a limitation. While some embodiments have been shown and described, it will be apparent to those skilled in the art that modifications may be made without departing from the broader aspects of the technological contribution. The actual scope of the protection sought is intended to be defined in the following claims.

What is claimed is:

1. A staple instrument comprising:
   a staple holder;
   a rotational drive shaft;
   an articulated linkage operatively coupled to the staple holder to expand the staple holder; and
   a converter coupling intermediate the rotational drive shaft and the articulate linkage to convert rotational motion of the rotational drive shaft to linear motion for the articulated linkage;
   wherein the staple holder includes at least a first jaw and a second jaw, and the articulated linkage includes at least a first link and a second link, and the first jaw being attached to the first link and the second jaw being attached to the second link;
   wherein the first jaw is offset from the first link and the second jaw is offset from the second link;
   wherein a first angle between the first jaw and the first link defines a first offset and a second angle between the first jaw and the second jaw defines a second offset; and
   wherein the first angle and the second angle are equal.

2. The staple instrument of claim 1 wherein the articulated linkage includes a third link connected to the converter coupling and the first link.

3. The staple instrument of claim 2 wherein the third link is pivotally connected to the converter coupling.

4. The staple instrument of claim 3 wherein the third link is pivotally connected to the first link.

5. The staple instrument of claim 4 further comprising a fourth link being pivotally coupled to the second link.

6. The staple instrument of claim 1 further comprising a housing.

7. The staple instrument of claim 6 wherein the articulated linkage is coupled to the housing.

8. The staple instrument of claim 6 wherein the rotational drive shaft is coupled to the housing.

9. The staple instrument of claim 6 wherein the housing defines a plurality of holes.

10. The staple instrument of claim 6 wherein the housing defines a yoke and the articulated linkage operates at least in part in the yoke.

11. The staple instrument of claim 1 wherein the drive shaft includes a first position being engaged with the converter and a second position being disengaged from the converter.

12. The staple instrument of claim 11 wherein the second position provides a spacing between the drive shaft and the converter.

13. The staple of claim 1 wherein the staple holder includes an edge for engaging a bridge of a staple inserted in a bone.

14. The staple instrument of claim 13 wherein the staple holder includes an arcuate surface for engaging bone to pry a staple from the material using the edge.

15. A kit comprising:
    a container; and
    a staple instrument in the container, the staple instrument comprising:
      a staple holder
      a rotational drive shaft;
      an articulated linkage operatively coupled to the staple holder to expand the staple holder; and
      a converter coupling intermediate the rotational drive shaft and the articulate linkage to convert rotational motion of the rotational drive shaft to linear motion for the articulated linkage;
      wherein the staple holder includes at least a first jaw and a second jaw, and the articulated linkage includes at least a first link and a second link, and the first jaw being attached to the first link and the second jaw being attached to the second link;
      wherein the first jaw is offset from the first link and the second jaw is offset from the second link;
      wherein a first angle between the first jaw and the first link defines a first offset and a second angle between the first jaw and the second jaw defines a second offset; and
      wherein the first angle and the second angle are equal.

16. The kit of claim 15 further comprising at least one drill guide.

17. The kit of claim 15 further comprising at least one staple.

* * * * *